United States Patent [19]

Cook et al.

[11] 4,147,802

[45] Apr. 3, 1979

[54] METHOD OF TREATING BACTERIAL INFECTIONS

[75] Inventors: Elton S. Cook, Cincinnati, Ohio; Akira Fujii, Matsudo, Japan

[73] Assignee: Stanley Drug Products, Inc., Portland, Oreg.

[21] Appl. No.: 888,011

[22] Filed: Mar. 17, 1978

[51] Int. Cl.$^2$ .......................................... A61K 31/195
[52] U.S. Cl. .................................................. 424/319
[58] Field of Search ........................................ 424/319

[56] References Cited

PUBLICATIONS

Chemical Abstracts 62:13226 (d) (1965).

*Primary Examiner*—Jerome D. Goldberg
*Attorney, Agent, or Firm*—John G. Schenk

[57] ABSTRACT

A variety of substances are known which induce or alter host resistance to coccic and bacillic infections. It is also known that treatment is complicated by the ability of such organisms to develop resistance to antimicrobials. Numerous strains are known which elaborate enzymes in response to these drugs and thus remain insensitive to them. Hence there appears to be a never-ending demand for anti-coccic and anti-bacillic factors. Certain substituted para-aminobenzoic acids are shown herein to render the host immune to such strains.

6 Claims, No Drawings

METHOD OF TREATING BACTERIAL INFECTIONS

BACKGROUND OF THE INVENTION

This invention pertains to antimicrobials effective in protecting against cocci and bacilli bacterial infections.

Although many antimicrobials have been suggested for the treatment of cocci and baccilic infections, such diseases continue to be a problem. The reason for this is that bacteria such as cocci and bacilli are a unique group of organisms embodying within themselves an array of yet unanswered puzzles in biology, both fundamental and experimental. They are ubiquitous in distribution and have attained extreme degrees of diversification in biological and biochemical characteristics. It is recognized that the significance of staphylococcal infections is not so much in severity, except in a few instances, as in the subtleties of the infection due to the unpredictable vagaries of these organisms.

Treatment of bacterial diseases caused by cocci and baccili is complicated by the ability of the organisms to develop resistance. The magnitude of the problem is further amplified by the extreme difficulty of total eradication, and the frequent reappearance of the same strain even after apparently successful elimination. The inability to eliminate the carrier state by any of the currently known methods and the prevalence of the new antibiotic resistant hospital strains have added a new dimension to the frustrating situation. The development of such multiple antibiotic resistant strains of the organism suggests the desirability of investigating additional means of combatting the infections. As a consequence the development of antimicrobials which are effective against coccic and bacillic infections has attracted considerable attention.

SUMMARY OF THE INVENTION

In accordance with the practice of this invention a new antimicrobial is provided conferring on mammals remarkable resistance to coccus and bacillus infections. The approach is to administer to a mammal suffering from said bacterial infection an antibacterial effective amount of an omega-aminoacyl-para-aminobenzoic acid. The invention thus provides an antimicrobial effective in inducing resistance to bacterial infections, without the necessity of infection by the organisms.

DETAILED DESCRIPTION OF THE INVENTION

The processes of injection leading to coccic infections are accepted to be problems in the ecology of the parasite. It is being increasingly realized that the bacterial and host determinants are closely interrelated. Staphylococcal virulence derives from the combined action of several bacterial factors whose effectiveness is conditioned by the reactions of the host. Perhaps the most striking feature of host-parasite relationships in staphylococcal infections is the relatively atypical immumologic response. Human studies have given convincing evidence that most adult humans possess an array of anti-staphylococcal antibodies. Nevertheless resistance to staphylococcal infections seems to be governed to a considerable extent by other unrelated factors. For example, in the true sense the compounds employed herein are not antibiotics. In vitro tests show that these compounds do not kill the organism. However, quite surprisingly, in the system of the host they create an environment in which the organism does not grow. For this reason the compounds are called probiotics. The term probiotics has been proposed to designate compounds which build resistance to infection in the host, but do not inhibit the growth of microorganisms in vitro. Thus they unexpectedly render immunity to the host, as does a vaccine, but without the organism itself being present as it is in vaccines.

The compositions of this invention thus constitute a significant new class of antimicrobials. Specifically they are para-substituted benzoic acids having the formula

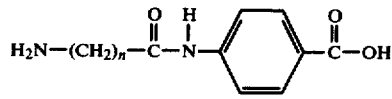

wherein n is a natural number 1 through 5. It is contemplated that they will be taken orally, or by intra-muscular injection.

The probiotics with which this invention is concerned, hence, are aminoethanoyl-p-aminobenzoic acid, $\beta$-aminopropanoyl-p-aminobenzoic acid, $\gamma$-aminobutanoyl-p-aminobenzoic acid, $\delta$-aminopentanoyl-p-aminobenzoic acid and $\epsilon$-aminohexanoyl-p-aminobenzoic acid. These p-aminobenzoic acids were prepared by the carbobenzoxy method. Thus, the carbobenzoxy-$\omega$-amino acid was reacted with ethyl chloroformate to form an activated carboxylic acid function, which was then treated with ethyl p-aminobenzoate to obtain ethyl carbobenzoxy-$\omega$-aminoacyl-p-aminobenzoate. After the hydrolysis by dilute sodium hydroxide, the carbobenzoxy-$\omega$-aminoacyl-p-aminobenzoic acid was hydrogenated in the presence of palladium black (10% Pd/C) to produce the $\omega$-aminoacyl-p-aminobenzoic acid. The crude product was purified by means of ion exchange chromatography.

The high degree of resistance to staphylococcal infections obtained by these para-substituted benzoic acids will best be apparent from their biological effects in in vivo tests. In these in vivo tests antistaphylococcal activity was determined using BDF mice, both male and female. The animals were between 9 and 13 weeks old, males having approximate average weights of 12 and 19 grams, females 18 to 24 grams. For the most part the mice were raised and maintained on the Rockland diet.

The assays were conducted using a penicillin-resistant strain, *Staphylococcus aureus* Original, first isolated from a case of acute tonsilitis and maintained in our laboratories for years. This strain is preserved in the lyophilized form and stored at 0° C., and stock cultures were raised on SA 110 slants once in every 6 months. For testing, the inoculum was prepared as 24 hour cultures from Bacto-Staphylococcus Medium 110. The cells were washed and suspended in physiological saline (TC Tyrode Solution, Difco). In contrast to conventional procedures, a dose killing 80 to 90 percent ($LD_{80-90}$) instead of a dose killing 50 percent ($LD_{50}$) was used in these investigations. This has been the practice in our laboratories in studies with staphlococci since lower dosages often fail to give adequate degrees of morality. The $LD_{80-90}$ was determined by injecting groups of mice subcutaneously with different dilutions of the bacterial suspension and noting the mortality over a 5-day period.

Using groups of twenty-two to twenty-four mice, the animals were inoculated subcutaneously two hours before and four hours after challenge with a 60 percent suspension of the "Original Strain" organism. Antistaphylococcal activity was determined using 1 mg doses per mouse of the omega-aminoacyl-p-aminobenzoic acid. Such antistaphylococcal activity in vivo is expressed as ASA and as effectiveness of protection using the $\chi^2$-test, ASA being determined by ASA=$[(M_c-M_e)/M_c]/C$, where $M_c$ is the mortality of untreated negative control animals, $M_e$ is the mortality of the experimental animals, and C is the dose in millimols. Results of the tests are given in the following table.

ANTISTAPHYLOCOCCAL ACTIVITY

| Antimicrobial | Percent Protection per Millimole (ASA) |
|---|---|
| aminoethanoyl-p-aminobenzoic acid | 12.71 |
| β-aminopropanoyl-p-aminobenzoic acid | 20.72 |
| γ-aminobutanoyl-p-aminobenzoic acid | 29.66 |
| δ-aminopentanoyl-p-aminobenzoic acid | 31.53 |
| ε-aminohexanoyl-p-aminobenzoic acid | 49.47 |

The table shows the antistaphylococcal activity to be superior to the untreated negative control. Moreover ε-aminohexanoyl-p-aminobenzoic acid was particularly effective, being the most potent antistaphylococcal agent. None of the ω-aminoacyl-p-aminobenzoic acids inhibited the growth of Staphylococcus aureous in vitro.

The compositions of this invention thus constitute a significant new class of antistaphylococcal agents. It is contemplated that they will be taken orally, say 250 to 500 milligram tablets. Where exposure to staphylococci or streptococci infections is likely, such as on entering a hospital, injections of say, 150 to 500 mg, will be prescribed. The para-aminobenzoic acid derivatives can be combined with an aqueous vegetable, monoglyceride or diglyceride vehicle for injection, sodium chloride being used if necessary to render the solution isotonic. The suspension or solution will contain 0.1 to 5 percent, preferably 0.1 to 1.5 percent of the antimicrobial by weight.

In the case of tablets, if desired, suitable colorants, adhesives, and lubricants will be incorporated along with a solid pharmaceutical diluent, for instance, starches, lactose, sucrose, and other pharmaceutical diluents. These tablets will contain 50 percent of the p-aminobenzoic acid compound on a weight basis. Capsules can also be made. Thus a process is provided for the control of infections in humans and other mammals due to cocci which involves administering to the mammal an effective amount of the para aminobenzoic acid compound. Various diluents, doses, and other variations and modifications will occur to those skilled in the art. Thus it has been pointed out that tablets must be administered more frequently than injections. Such ramifications are deemed to be within the scope of this invention.

What is claimed is:

1. A method of treating bacterial infections in mammals comprising administering to a mammal suffering from said bacterial infection an antibacterial effective amount of a para-substituted benzoic acid having the formula

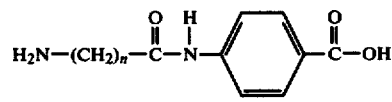

wherein n is a natural number 1 through 5.

2. The method of claim 1 wherein the para-substituted benzoic acid is aminoethanoyl-p-aminobenzoic acid.

3. The method of claim 1 wherein the para-substituted benzoic acid is β-aminopropanoyl-p-aminobenzoic acid.

4. The method of claim 1 wherein the para-substituted benzoic acid is γ-aminobutanoyl-p-aminobenzoic acid.

5. The method of claim 1 wherein the para-substituted benzoic acid is δ-aminopentanoyl-p-aminobenzoic acid.

6. The method of claim 1 wherein the para-substituted benzoic acid is ε-aminohexanoyl-p-aminobenzoic acid.

* * * * *